(12) United States Patent
Melen

(10) Patent No.: US 6,208,709 B1
(45) Date of Patent: Mar. 27, 2001

(54) DETECTION PROCESSING SYSTEM

(75) Inventor: Robert E Melen, Saratoga, CA (US)

(73) Assignee: Cardiac Mariners, Inc., Los Gatos, CA (US)

( * ) Notice: Subject to any disclaimer, the term of this patent is extended or adjusted under 35 U.S.C. 154(b) by 0 days.

(21) Appl. No.: 09/167,397

(22) Filed: Oct. 6, 1998

(51) Int. Cl.[7] .................................................. H05B 1/64
(52) U.S. Cl. ................................... 378/98.2; 378/98.12
(58) Field of Search .............................. 378/4, 98.2, 98.3, 378/98.8, 98.12, 146

(56) References Cited

U.S. PATENT DOCUMENTS

| | | | |
|---|---|---|---|
| 2,638,554 | 5/1953 | Bartow et al. | 250/99 |
| 2,667,585 | 1/1954 | Gradstein | 250/61.5 |
| 3,780,291 | 12/1973 | Stein et al. | 250/36.3 |
| 3,818,220 | 6/1974 | Richards | 250/61.5 |
| 3,925,660 | 12/1975 | Albert | 250/272 |
| 3,944,833 | 3/1976 | Hounsfield | 250/367 |
| 3,946,234 | 3/1976 | Hounsfield | 250/363 |
| 3,949,229 | 4/1976 | Albert | 250/401 |
| 3,983,397 | 9/1976 | Albert | 250/406 |
| 4,002,917 | 1/1977 | Mayo | 250/445 |
| 4,007,375 | 2/1977 | Albert | 250/404 |
| 4,010,370 | 3/1977 | LeMay | 250/366 |
| 4,031,395 | 6/1977 | LeMay | 250/360 |
| 4,032,787 | 6/1977 | Albert | 250/402 |
| 4,048,496 | 9/1977 | Albert | 250/272 |
| 4,052,619 | 10/1977 | Hounsfield | 250/363 |
| 4,057,745 | 11/1977 | Albert | 313/55 |
| 4,066,902 | 1/1978 | LeMay | 250/363 |
| 4,104,526 | 8/1978 | Albert | 250/403 |
| 4,144,457 | 3/1979 | Albert | 250/445 |
| 4,149,076 | 4/1979 | Albert | 250/402 |
| 4,196,351 | 4/1980 | Albert | 250/416 |
| 4,259,582 | 3/1981 | Albert | 250/402 |
| 4,259,583 | 3/1981 | Albert | 250/416 |
| 4,260,885 | 4/1981 | Albert | 250/277 |
| 4,288,697 | 9/1981 | Albert | 250/505 |
| 4,321,473 | 3/1982 | Albert | 250/505 |
| 4,323,779 | 4/1982 | Albert | 250/401 |
| 4,464,776 | 8/1984 | Erker | 378/10 |
| 4,465,540 | 8/1984 | Albert | 156/252 |
| 4,519,092 | 5/1985 | Albert | 378/45 |
| 4,573,179 | 2/1986 | Rutt | 378/10 |
| 4,730,350 | 3/1988 | Albert | 378/10 |
| 5,122,422 | 6/1992 | Rodhammer et al. | 428/634 |
| 5,267,296 | 11/1993 | Albert | 378/113 |
| 5,293,417 | 3/1994 | Wei et al. | 378/147 |
| 5,463,668 | * 10/1995 | Kagaya | 378/98.12 X |
| 5,490,197 | * 2/1996 | Albert et al. | 378/137 X |
| 5,550,378 | 8/1996 | Skillicorn et al. | 250/367 |
| 5,608,774 | * 3/1997 | Polichar et al. | 378/98.8 |
| 5,644,612 | 7/1997 | Moorman et al. | 378/98.2 |

FOREIGN PATENT DOCUMENTS

| | | | |
|---|---|---|---|
| WO 94/23458 | 10/1994 | (WO) | H01L/31/115 |
| WO 96/25024 | 8/1996 | (WO) | H05J/35/00 |

OTHER PUBLICATIONS

Curry et al., *Christensen's Physics of Diagnostic Radiology*, Fourth Edition, Lea & Febiger, 1990, pp. 1–522.

(List continued on next page.)

*Primary Examiner*—David P. Porta
(74) *Attorney, Agent, or Firm*—Lyon & Lyon LLP

(57) ABSTRACT

A system for scanning an x-ray target in an x-ray imaging system with a charged particle beam. The system for scanning comprises deflecting the charged particle beam to re-illuminate the portion of the object to be imaged in a time period that is sufficiently small to prevent image blurring during image reconstruction. The system for scanning further comprises a scan processing system for processing x-ray transmissiveness information received as a result of a scanning pattern that re-illuminates an object.

17 Claims, 7 Drawing Sheets

OTHER PUBLICATIONS

Moon, "Amplifying and Intensifying the Fluroscopic Image by Means of a Scanning X–ray Tube", Oct. 6, 1950, *Science*, vol. 112, pp. 389–395.

Skillicorn, "Insulators and X–ray Tube Longevity: Some Theory and a Few Practical Hints", *Kevex*, Jun., 1983, pp. 2–6.

Howard Pattee, Jr., "Possibilites of the Scanning X–Ray Microscope", at least by Dec., 1957, *X–Ray Microscopy and Microradiography*, pp. 367–375.

Philips Photonics, "XP1700 Multichannel Photomultipliers", *Xp1700 Family of Multi–channel Photomultipliers–Philips Photonic Handbook*, at least by Dec. 1993, pp. 1–15.

Pattee, "The Scanning X–ray Microscope", Jan. 1953, *Journal Opt. Soc. Amer.*, vol. 43, pp. 61–62.

* cited by examiner-

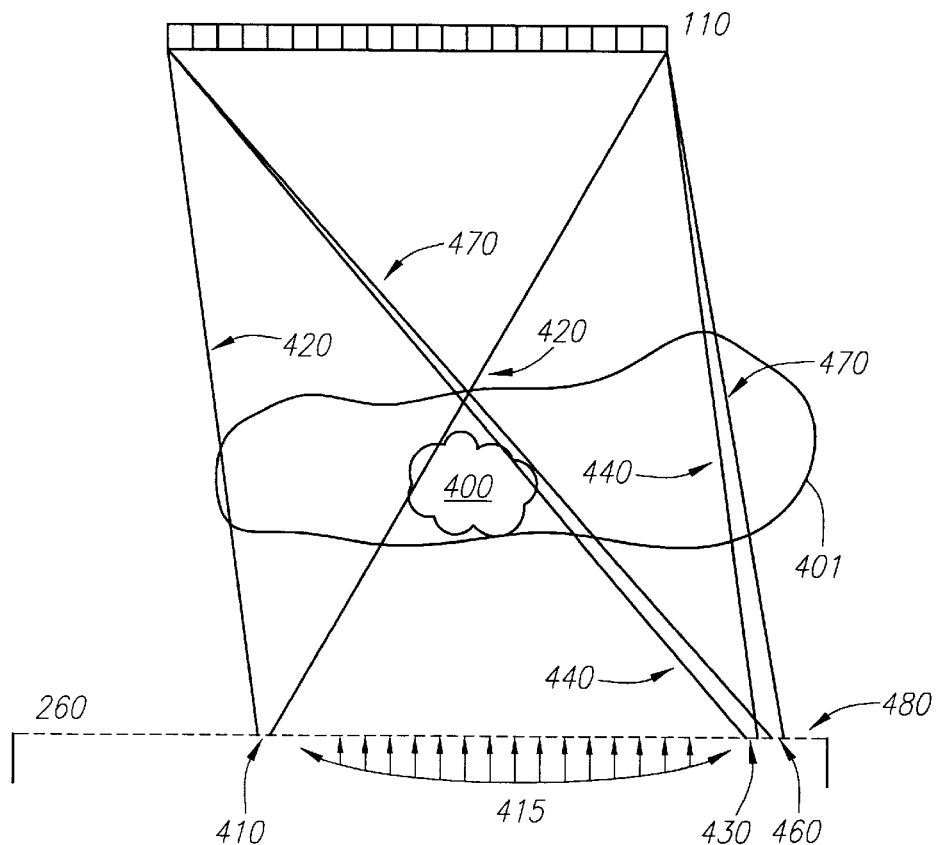
FIG. 4
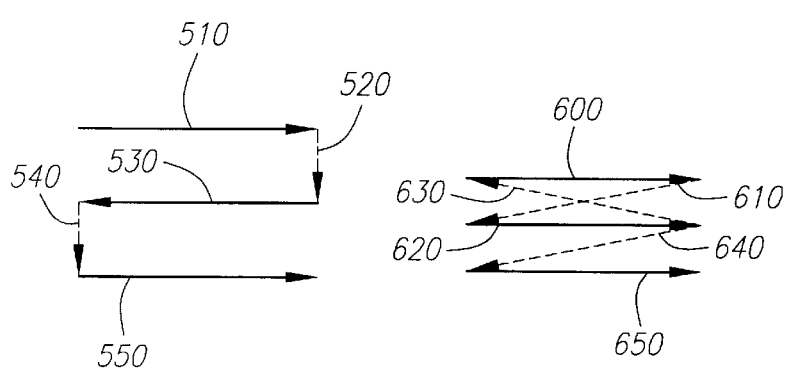
FIG. 5
FIG. 6
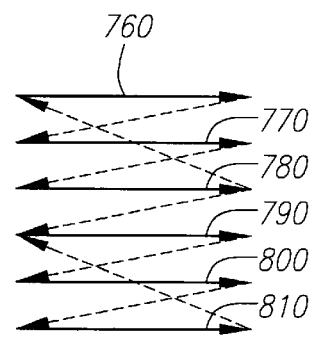
FIG. 7

DETECTION PROCESSING SYSTEM

BACKGROUND

1. Field of the Invention

The field of the present invention pertains to diagnostic x-ray imaging equipment, including among other things, real-time x-ray imaging methods and apparatus.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modem medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. Scanning x-ray tubes have been known in conjunction with the fluoroscopy art since at least the early 1950s. Moon, *Amplifying and Intensifying the Fluoroscopic Image by Means of a Scanning X-ray Tube*, Science, Oct. 6, 1950, pp. 389–395.

Another approach to x-ray imaging involves the use of reverse-geometry x-ray imaging systems. In such systems, an x-ray tube is employed in which an electron beam is generated and focussed upon a small spot on a relatively large target assembly, emitting x-ray radiation from that spot. The electron beam is deflected in a scan pattern over the target assembly. A relatively small x-ray detector is placed at a distance from the target assembly of the x-ray tube. The x-ray detector converts x-rays that strike it into an electrical signal indicative of the amount of x-ray flux detected at the detector. One advantage provided by reverse-geometry systems is that the geometry of such systems allows x-rays to be projected at an object from multiple angles without requiring physical relocation of the x-ray tube.

When an object is placed between the x-ray tube and the detector, x-rays are attenuated and/or scattered by the object in proportion to the x-ray density of the object. While the x-ray tube is in scanning mode, the signal from the detector is inversely proportional to the x-ray density of the object. The output signal from the detector can be applied to the z-axis (luminance) input of a video monitor. This signal modulates the brightness of the viewing screen. The x and y inputs to the video monitor can be derived from the signals that effect deflection of the electron beam of the x-ray tube. Therefore, the luminance of a point on the viewing screen is inversely proportional to the absorption of x-rays passing from the source, through particular areas of the object, to the detector.

Medical x-ray systems are usually operated at the lowest possible x-ray exposure level at the entrance of the patient that is consistent with image quality requirements (particularly contrast resolution and spatial resolution requirements for the procedure and the system being used).

Time and area distributions of x-ray flux follow a Poisson distribution and have an associated randomness. The randomness is typically expressed as the standard deviation of the mean flux and equals its square root. The signal-to-noise ratio of an x-ray image under these conditions is equal to the mean flux divided by the square root of the mean flux, i.e., for a mean flux of 100 photons, the noise is +/−10 photons, and the signal-to-noise ratio is 10.

A relatively high level of x-ray flux makes it easier to yield high resolution images. A high level of x-ray flux can create a potentially more accurate image by decreasing the x-ray quantum noise. The x-ray flux should be projected through the object often enough to allow a frame rate (the number of times per second that an object is scanned and the image refreshed) which produces an acceptable image picture and refresh rate at a video display device.

In a reverse-geometry medical imaging system, the desire for high levels of x-ray flux normally requires extended bombardment of an x-ray tube target assembly by a high energy electron beam. In creating x-rays in response to an electron beam, the x-ray target assembly is raised to high temperatures; in some systems, the target assembly material is heated to temperatures in excess of 1000 degrees centigrade. Prolonged exposure of the target assembly to high temperatures can cause melting or cracking of the target assembly material due to thermal stress. Even if the prolonged exposure does not immediately cause the target assembly material to fail, such exposure can cause long-term damage that affects the longevity of the target assembly.

Thus, several conflicting factors, among them image resolution, frame rate, and the thermal qualities of x-ray target assembly materials, may work to limit the usefulness of conventional x-ray imaging systems. Maintaining an electron beam bombardment of an x-ray tube target assembly for a sufficient period of time to satisfy flux/frame rate requirements may result in damage to the target assembly material. However, reducing the flux/frame rate requirement to prevent damage to the target assembly may result in diminished image quality.

Therefore, there is a need for an x-ray imaging method and system that is capable of addressing the shortcomings of the prior approaches. There is a need for a method and system that can provide a high level of x-ray flux to each portion of an object being imaged during a short period of time while preventing damage to the target material and increasing target longevity.

SUMMARY OF THE INVENTIONS

The present invention comprises a system and method for scanning a charged particle beam across a target assembly in an x-ray source to emit x-ray beams to generate an image of an object. An aspect of the invention comprises moving an electron beam over certain positions on the target assembly more than once per image frame in order to increase the flux provided to each portion of the object to be imaged, while at the same time increasing target longevity.

Another aspect of the invention comprises a scanning system for processing x-ray transmissiveness information that results from rescanning portions of a target assembly. According to one feature of this aspect, the scanning system comprises circuitry to combine two or more pieces of x-ray transmissiveness information, that relate to the same relative detector xray source locations, into a single combined piece of x-ray transmissiveness information.

These and other objects and aspects of the present inventions are taught, depicted and described in the drawings and the description of the invention contained herein.

BRIEF DESCRIPTION OF THE DRAWINGS

FIG. 4 is a diagram of x-ray paths emanating from a row of apertures that pass through an object and cover the multi-detector array.

FIG. 5 is a diagram of a stepping pattern of an electron beam across a target assembly.

FIG. 6 is a diagram of an alternate stepping pattern of an electron beam.

FIG. 7 is a diagram of an alternate stepping pattern of an electron beam.

DESCRIPTION OF THE PREFERRED EMBODIMENTS

System Overview

Figure 1:
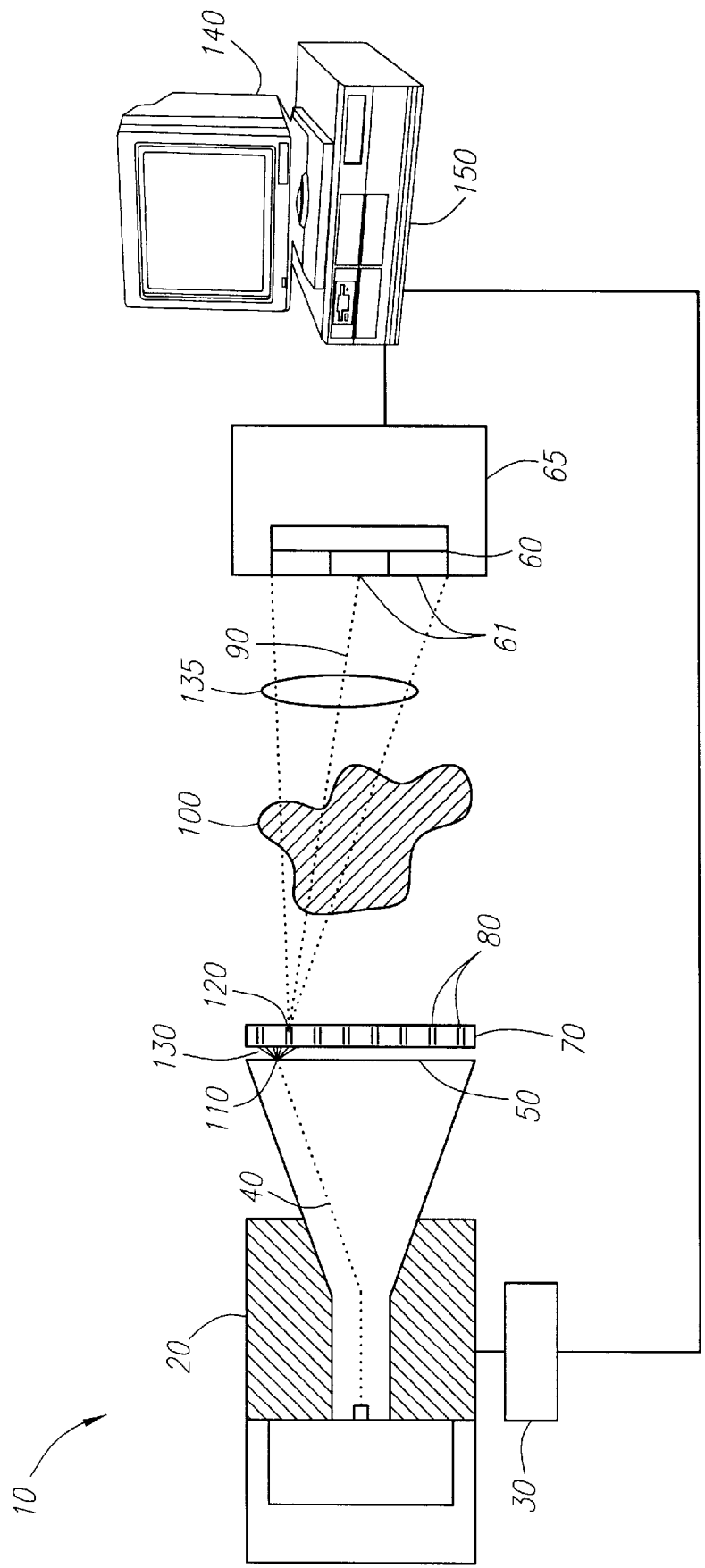
FIG. 1 is a block diagram showing components of one embodiment of an x-ray imaging system according to the present inventions.

FIG. 1 is a diagram showing the high level components of an embodiment of a x-ray imaging system according to the invention. X-ray source 10 includes an electron beam source comprising a power supply which can operate x-ray source 10 at about −70 kV to −120 kV. In the present embodiment, this voltage level produces a spectrum of x-rays ranging to 120 keV. Electron beam 40, which is generated within x-ray source 10 by a charged particle gun, is deflected over the surface of a target assembly 50 (which is a grounded anode in an embodiment of the invention) in a predetermined pattern, e.g., a scanning or stepping pattern. X-ray source 10 includes a mechanism to control the movement of electron beam 40 across target assembly 50, such as a deflection yoke 20 under the control of an electron beam pattern generator 30.

A preferred x-ray source 10 is disclosed in copending U.S. patent application Ser. Nos. 09/167,329 and 09/167,524, filed concurrently with the present application, both of which are incorporated by reference in their entirety. A method and apparatus for generating and moving electron beam 40 across target assembly 50 is disclosed in commonly owned U.S. Pat. No. 5,644,612 which is incorporated herein by reference in its entirety.

In FIG. 1, a collimating assembly is located between target assembly 50 of x-ray source 10 and a multi-detector array 60. In the preferred embodiment, the collimating assembly is located between target assembly 50 and the object 100 for which an image is to be obtained. The presently preferred collimating assembly is collimator grid 70, containing a plurality of x-ray transmissive apertures 80 arranged in a grid pattern. Collimator grid 70 is designed to permit passage of x-rays forming a diverging beam 135 that directly intercepts multi-detector array 60. In an embodiment, collimator grid 70 utilizes a cooling assembly and beam hardening filters. Examples of preferred collimator grids and beam hardening filters that can be utilized in the invention include these depicted and disclosed in U.S. Pat. No. 5,610,967 and copending U.S. patent application Ser. No. 09/167,639 filed concurrently with the present application, both of which are hereby incorporated by reference in their entirety.

In operation, electron beam 40 preferably dwells at location 110 on target assembly 50 which is located substantially at a position where the axis 90 for a particular aperture 120 of collimator grid 70 intersects the target assembly 50. As the electron beam 40 strikes target assembly 50 at location 110, a cascade of x-rays 130 is emitted. Only the portion of the cascade of x-rays 130 whose path lies substantially along axis 90 pass through aperture 120 and form a diverging x-ray beam 135. The shape of x-ray beam 135 is influenced by the shape of aperture 120. For instance, if the aperture is square the x-ray beam 135 takes on a generally truncated pyramidal shape. If the aperture is circular, x-ray beam 135 takes on a generally conical shape. In a preferred embodiment, the shape and area of the aperture is such that the area of maximum divergence of the x-ray beam 135 is substantially the same as the dimensions of the x-ray capture surface for multi-detector array 60.

Multi-detector array 60 comprises a plurality of discrete detectors (referred to herein as "detector elements") 61 arranged in an array. Each detector element 61 includes a x-ray surface having a capture area for detecting x-rays. Each detector element is capable of independently measuring the amount of x-rays that strike it. When an object 100 is interposed between the x-ray source 10 and the multi-detector array 60, some of the x-rays in x-ray beam 135 will pass through a portion of object 100, and if not scattered or absorbed, will strike the detector elements that make up multi-detector array 60. The x-rays that strike any individual detector element comprise a portion of x-ray beam 135 that is referred to herein as an x-ray beam subpath.

In a preferred embodiment, each detector element comprises components for measuring the quantity of x-ray photons that strike the detector element and outputting a signal representative of that measurement. Alternatively, each detector element includes components for generating an electrical signal generally proportional to the total energy of the x-rays that strike the detector element. The magnitude of the generated electrical signals corresponds to the flux intensity of the x-rays from the detected x-ray beam subpath of x-ray beam 135. Utilizing a multi-detector array 60 that independently measures the x-rays which strike each detector element results in the generation of x-ray transmissiveness information that is proportional to the x-ray flux passing through object 100 along particular x-ray beam subpaths. The resulting intensity data can be used or manipulated to create a representation of object 100, i.e. a representation of the x-ray transmissiveness of object 100, which can be displayed on monitor 140.

X-ray transmissiveness information obtained from the detector elements 61 pertinent to specific image pixels are reconstructed by image reconstruction system 65. In an embodiment, image reconstruction system 65 also performs control functions and display preparation for the x-ray imaging system. Operational instructions and control of the x-ray source 10, detector 60 and image reconstruction system 65 are made through a control workstation 150. Control workstation 150 also receives operational and status information from the various components of the x-ray imaging system.

Figure 8:
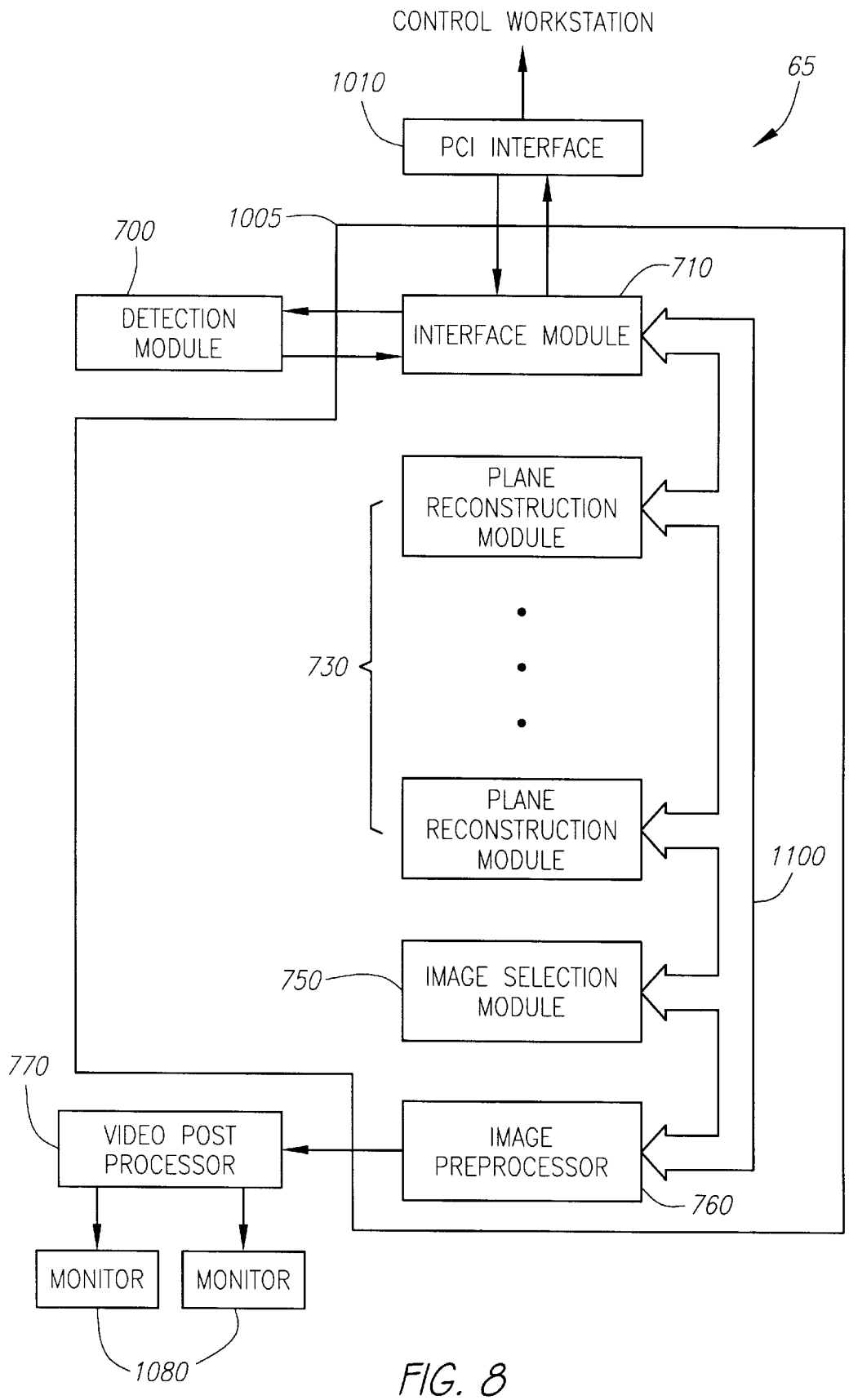
FIG. 8 is a block diagram showing the components of an embodiment of an image reconstruction system.

FIG. 8 depicts a block diagram of an embodiment of image reconstruction system 65. The image reconstruction system 65 comprises a PCI interface 1010 which connects to control workstation 150. In an embodiment, a detection module 700 comprises the components of multi-detector array 60 and receives x-ray transmissiveness information. Alternatively, multi-detector array 60 is physically separate from the image reconstruction system 65 and the detection module 700 comprises components to receive data signals from the multi-detector array 60. Image reconstruction chassis 1005 comprises an interface module 710, one or more plane reconstruction modules 730, an image selection module 750 and an image preprocessor 760. The various components on the image reconstruction chassis 1005 are interconnected via one or more busses 1100, which also include control lines. Video post processor 770 is coupled to display monitors 1080. An image construction system and method is disclosed in copending U.S. patent application Ser. No. 09/167,413 and application Ser. No. 09/167,171, filed concurrently herewith, which are hereby incorporated by reference in their entirety.

Figure 2:
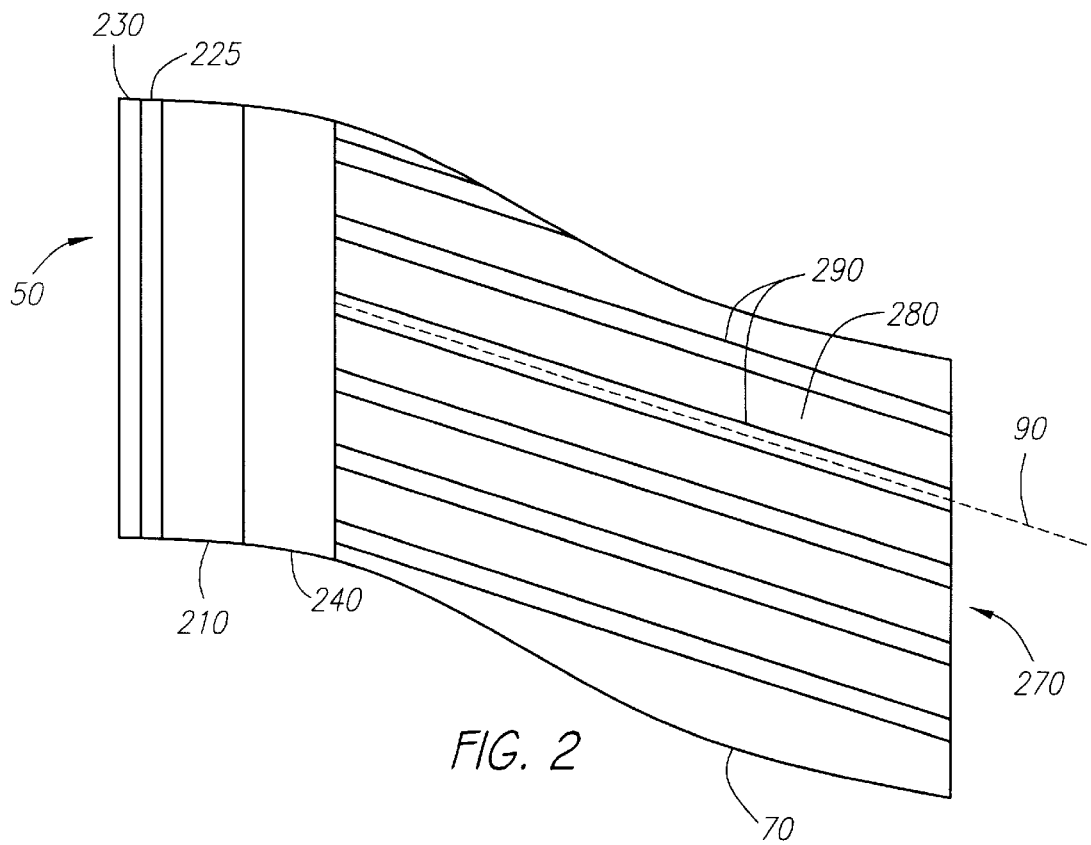
FIG. 2 is an enlarged cross-sectional view of a portion of a collimation grid and target assembly for use in an imaging system.

Referring to FIG. 2, shown is an embodiment of a target assembly 50 that can be used in the present invention. Target assembly 50 comprises an x-ray generating layer 230 which is supported by a support layer 210. A thermal buffer 225 can be disposed between the x-ray generating layer 230 and the support layer 210. The preferred target assembly is disclosed in more detail in U.S. patent application Ser. No. 09/167,413 and application Ser. No. 09/167,171 filed concurrently with the present application, which is hereby incorporated by reference in its entirety.

In FIG. 2, a cooling chamber 240 is located between the target support 210 and collimation grid 70. A cooling fluid can be allowed to flow within cooling chamber 240 to cool the target assembly 50. Collimation grid 70 comprises a plurality of x-ray transmissive apertures 290.

According to an embodiment, the central axis 90 of each of the apertures 290, is aligned with center of the multi-detector array 60 (FIG. 1). In other words, the axes of apertures within the collimation grid 70 are not parallel to each other, but form an acute angle to a line perpendicular to the output face 270 of the collimation grid 70. For example, an embodiment of a collimation grid for a chest x-ray application comprises apertures forming an angle with a line perpendicular to the output face 270 of the collimation grid 70 of between 0° at the center of the collimation grid 70 to as much as 20° at the edge of the grid 70. A mammogram application on the other hand may have a collimation grid 70 comprising apertures forming an angle with a line perpendicular to the output face 250 ranging to 45° at the edge of the grid. Thus, a preferred scanning beam x-ray imaging system allows different collimation grids to be selected and used depending on the particular medical application.

X-ray absorbent portion 280 of collimation grid 70 is designed to absorb errant x-rays so that they do not irradiate the object. This is accomplished by fabricating the preferred collimation grid 70 with sufficient thickness so that the x-ray radiation passing through an aperture 290 towards the multi-detector array 60 is substantially greater than the cumulative x-ray radiation passing through x-ray absorbent portion 280 in all directions other than toward the multi-detector array 60. Such errant x-rays would provide the patient and attending staff with x-ray dosage while contributing no meaningful information to the image.

Figure 3:
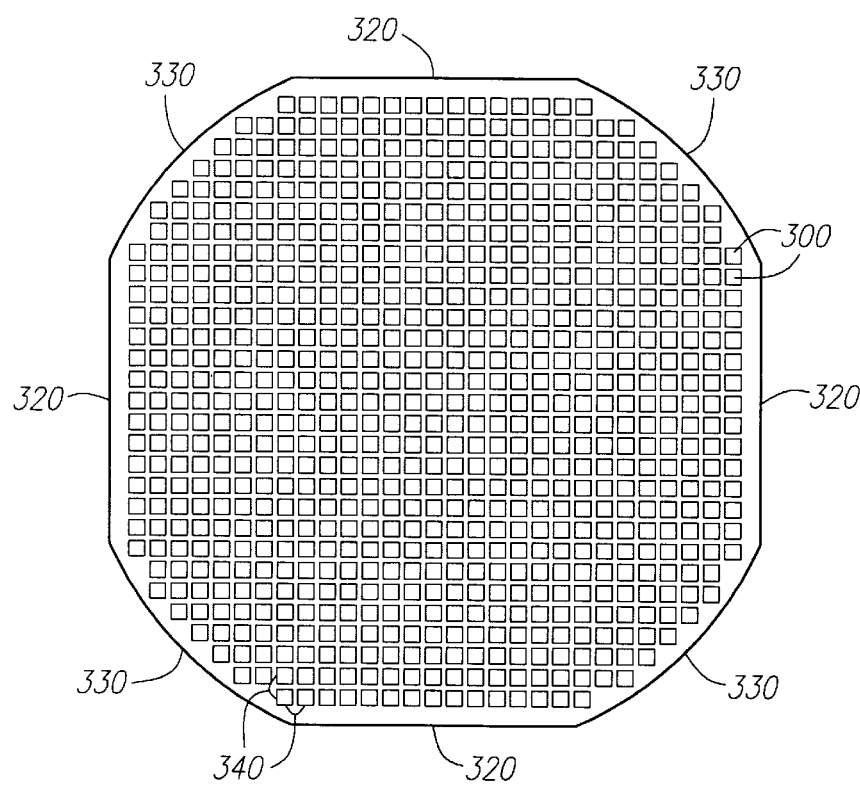
FIG. 3 is a front view of an embodiment of a collimation grid.

Referring to FIG. 3, collimation grid 70 is preferably of a shape resembling an octagon, with circular shaped portions 330 and straight line edges 320, although any shape that can be used in an x-ray scanning-beam system can be employed with the present invention. X-ray transmissive apertures 300 are arranged into a pattern of rows and columns. In an embodiment, the number of rows and columns is the same, so that the arrangement of x-ray apertures 300 is in the pattern of a square. Further, the pitch 340 between apertures 330 is the same for all apertures in both the horizontal and vertical directions. The dimensions of collimation grid are preferably ten (10) inches in diameter between circled shape portions 330 and a distance of nine (9) inches between the centers of straight line edges 320 and the preferred pitch 340 is between two (2.0) millimeters and two point five (2.5) millimeters. The size and shape of the apertures collimation grid that can be used with the present inventions are dependent on the material used in manufacturing the collimation grid as well as the particular application to which the invention are directed. The above described shape and size are not intended to be limiting in any way.

Scanning Method

To form an image for display, the electron beam 40 is stepped across the x-ray target assembly at positions opposing a group of apertures in the collimation grid that form a particular area of the collimation grid 70. X-ray transmissiveness information is measured at the multi-detector array 60 for x-rays emanating through each of the apertures. The measured x-ray transmissiveness information is mathematically combined to generate image data.

In an embodiment of an imaging system for medical applications, at least 15 and preferably 30 frames per second should be produced. A frame is a complete image, where all apertures that are required to emit x-rays do emit x-rays that provide information to the multi-detector array, from which an image is reconstructed. For a preferred embodiment using a 100 by 100 aperture collimation grid, the time for completing a scan of all of the positions on the target assembly for a single frame ranges from approximately 66.7 milliseconds (15 frames per second) to approximately 33.3 milliseconds (30 frames per second). Although the total frame time can range from 33 to 67 milliseconds, any object in the field of view of the x-ray source 10 is preferably illuminated for less than 12 milliseconds to minimize motion blurring that can result from motion within the object. When the x-ray imaging system is being utilized for cardiac imaging applications, objects within the field of view of x-ray source 10 are preferably illuminated for less that 4 milliseconds.

During operation, the electron beam is dwelled at a position on the target assembly for a fixed time period, which is referred to as a dwell time ($T_{Dwell}$), and is then deflected from the current dwelling position to a next dwelling position on the target assembly. Dwelling the electron beam at a position and then deflecting the electron beam to a next position is referred to as a step. During each dwell time, one x-ray path from an aperture passes through and illuminates a portion of the object and provides x-ray transmissiveness information about that portion of the object to the multi-detector array.

Referring to FIG. 4, an object 401 containing a smaller object or region of interest 400 is interposed between collimation grid 260 and multi-detector array 110. A first x-ray path 420 from aperture 410 in a row of apertures includes x-rays that travel through object of interest 400. A second x-ray path 440 from aperture 430 also includes x-rays that travel through object of interest 400. It can be seen that there are a number of apertures 415 between first aperture 410 and second aperture 430. A x-ray path from each of the apertures 415 includes x-rays that travel through object of interest 400 and provide information about object of interest 400 to the multi-detector array 110. However, a x-ray path 470 from aperture 460 does not include any x-rays that pass through object of interest 400. This is also the case for an x-ray path from aperture 480. X-rays emitted from apertures 460 and 480 will provide no meaningful information about object of interest 400 to the multi-detector array 110.

For any set of apertures used to illuminate an object of interest 400, the time between a dwell at the first aperture that illuminates the object of interest to a dwell at the last aperture is referred to as the illumination time ($T_{illumination}$). For the example depicted in FIG. 4, the time between a dwell at aperture 410 and at aperture 430, while also dwelling at each of the apertures 415 in between, is the illumination time ($T_{illumination}$) of the object of interest 400 which is in the field of view of an arrangement of multi-detector array 110 and collimation grid 260. As previously stated, the preferred illumination time for an object of interest in the field of view of the x-ray imaging system is less than 12 milliseconds and more preferably less that 4 milliseconds when the x-ray imaging system is being utilized for cardiac imaging applications.

An increased $T_{illuminatin}$ is achieved by stepping across an area of the target assembly corresponding to particular apertures more than once in creating each frame. The illumination of portions of an object more than once in a frame may be done for a number of purposes such as providing greater flux to the object for a clearer image while preventing target overheating of the target assembly materials. In restepping any portion of the target assembly, any part of the object that is imaged within a single image frame should not include normal motion that takes place within the body.

For instance, if a beating heart is being imaged, a second step at the same aperture that takes place too long after a first step will include imaging information with the heart in different positions. On a display the image of the heart will appear blurred. To prevent motion from being included in a single image frame, any portion of the object being imaged should be re-illuminated within a short enough time span to limit the introduction of motion into an image created within a single frame.

It is also preferred for maintenance and longevity of the target that the time between a first dwell time and a second dwell time at any particular position on the target assembly allows time for the target to sufficiently cool down after the first dwell time at that position on the target assembly. By creating the total desired flux over two x-ray emitting sessions separated by a period of time, the target is given an opportunity to cool down from the effects of the electron beam bombardment from the first dwell time prior to further electron beam bombardment from a second dwell time. In an embodiment, the period between the first dwell time and second dwell time is greater than 100 microseconds and is preferably at or greater than 300 microseconds. Alternate embodiments comprise the rescanning of particular portions of the target any number of times to generate the desired flux, including 3 or more scans through the same aperture in a single frame In an embodiment of an imaging system utilizing a tungsten-rhenium target assembly material, the dwell time at each position is approximately 1 microsecond, while the time for deflecting or sweeping the electron beam from one position to the next is approximately 280 nanoseconds. The dwell time should be limited to prevent excessive temperature rise in the target material which could damage the target assembly. Some factors used in determining the maximum dwell time ($T_{Dwell}$) are the material composition of the target assembly, including the melting point, specific heat and thermal conductivity of the target assembly materials, the electron beam power, and the size of the dwell spot on the target assembly.

Referring to FIG. 5, a pattern that can be used for stepping electron beam 40 across a target assembly 50 is a serpentine pattern or reversed "S" pattern. The serpentine pattern is generated by stepping the electron beam across first row 510 from a position on the target assembly opposing the left most aperture of the collimation grid to a position opposing the right most aperture, while dwelling at a position opposing each aperture in that row of the collimation grid. After dwelling at all of the desired dwelling positions in the first row 510, the electron beam is deflected to second row 530, adjacent to first row 510 along path 520. In stepping across second row 530 the electron beam dwells on the target assembly opposite the right most aperture and then continues for all desired positions opposing apertures in the row to left most aperture. After dwelling at all of the desired dwelling position in the second row 530, the electron beam is deflected to third row 550 along path 540. Third row 550 is stepped across in the same manner as first row 510, i.e., from left to right. This pattern is continued for the remainder of the target assembly. After stepping through each desired dwelling position, the data for a single image frame is completed. By stepping at desired dwelling positions opposite apertures in a preferred 100 by 100 collimation grid, an image of an area of an object can be constructed.

An embodiment of a stepping pattern where each position in a row is restepped is shown in FIG. 6. The electron beam is stepped along first row 600 in the same manner as in the reverse "S" pattern above. The electron beam is then preferably deflected over path 610, from a position opposing the right most aperture of first row 600 to a position opposing the left most aperture of the second row 620. After stepping across second row 620, the electron beam is preferably deflected, as shown by path 630, back to the left most position in first row 600, thereby allowing first row 600 to be stepped across a second time. Second row 620 is then stepped across again in the same manner as described above. The reverse "S" two row restepping pattern continues for each pair of desired rows of the target assembly, such that each desired pair of rows is stepped across twice before moving on to the next set of rows. Stepping across a single row in a preferred embodiment takes approximately 150 microseconds.

It may also be desired that the field of view to be imaged is less than the maximum field of view created by dwelling at dwelling positions behind the outer perimeter apertures in a collimation grid (which is a ten inch diameter for the preferred collimation grid). A smaller field of view can be created by scanning a smaller area of the target assembly (e.g., in a central area of the collimation grid that is smaller than the area of the entire grid). This can be accomplished, for example, by dwelling at dwelling positions within the area defined by the central 71 by 71 apertures of a collimation grid that has 100 by 100 apertures. In this arrangement the beam is preferably stepped across three adjacent rows twice prior to moving on to an adjacent set of three rows in a reverse "S" three row restepping pattern. One benefit of this scanning pattern is that it allows sufficient cool down time for each position on the target.

As shown in FIG. 7, row 760 is stepped across left to right starting from a dwelling position on the target opposing the left most aperture to a dwelling position on the target opposing the right most aperture. Row 770, and then 780, are thereafter stepped across in the same manner as row 760. After stepping across row 780, row 760 is restepped in the same manner it was originally stepped, followed by resteps across rows 770 and 780. Rows 790, 800 and 810 are then stepped across in the same manner as rows 760, 770 and 780. The pattern continues for all desired rows of the target opposite each row of apertures in the collimation grid.

For each of the above described stepping patterns, the preferred collimation grid comprised a square array of 100 by 100 apertures. The number of rows stepped prior to restepping the same number of rows is a function of balancing the cool down time $T_{Cool\ Down}$, which is dependent on the target material, and the time required to exclude motion in each portion of the image, which is dependent on the particular portion of the anatomy being imaged.

It is also possible to use the above described method to create a mini field of view. This is accomplished by stepping across an area on the target assembly the size of which corresponds to even fewer apertures in the collimation grid. For example, a mini field of view can be created by stepping across an area of the target assembly corresponding to a region of 50 by 50 apertures located in the central area of the preferred collimation grid. In this mini field of view, four rows are preferably stepped across once and then a second time, before going on to the next set of four rows creating a reverse "S" four row restepping pattern. Alternatively, the area to be scanned in the smaller and mini field of view image areas need not be in the central area of the collimation grid, nor does the area to be scanned necessarily need to be a square or rectangular shape.

An important factor in selecting a scanning pattern is that the time between dwells at a single position on the target assembly for an object in the field of view is selected such that all the positions on the target assembly that illuminate the object do so within a sufficient time period to eliminate blurring. In an embodiment, this time between dwells at a single position on the target assembly is also at least 100 microseconds and preferably 300 microseconds to prevent overheating at the target assembly. In practice, the smaller the field of view, the more rows that need to be stepped once prior to restepping any position within those rows. This is to maintain the time between steps of a same position in a row at a time period sufficiently long enough to prevent damage to the target.

Scan Processing System

The scan processing system of the present invention comprises components to efficiently process and receive x-ray transmissiveness information when portions of the object under examination are re-illuminated a plurality of times during a single frame. According to an embodiment of the invention, the scan processing system is a component of the detection module 700 shown in FIG. 8.

Referring back to FIG. 8, shown is a block diagram of an embodiment of image reconstruction system 65. Image reconstruction system 65 preferably comprises an image reconstruction chassis 1005, which comprises the components to reconstruct a display image from x-ray transmissiveness information received at the detection module 700. Components within an embodiment of image reconstruction chassis 1005 include an interface module 710 to receive x-ray transmissiveness information from detection module 700, one or more plane reconstruction modules 730 to reconstruct image pixels, an image selection module 750 to select image pixels for display, and an image preprocessor 760 to process image data for display.

According to an embodiment, detection module 700 is a component of the image reconstruction system 65. Alternatively, detection module 700 is physically and functionally separate from the image reconstruction system 65, and therefore detection module comprises components to send and receive data signals from the imaging chassis of image reconstruction system 65. In the embodiment shown in FIG. 8, detection module 700 comprises the components of multi-detector array 60 to detect x-ray transmissiveness information that passes through the object under examination. Alternatively, multi-detector array 60 is physically separate from the image reconstruction system 65 and the detection module 700 comprises components to receive and process data signals from the multi-detector array 60.

In operation, each time the electron beam dwells at a position on the target assembly associated with a particular aperture in the collimator, a complete set of data points, one for each detector element, is generated. For example, if the multi-detector array 60 comprises an array of 48×48 detector elements, and if the electron beam is dwelled at a particular location on the target for about 1.04 microseconds, with about 0.24 microseconds to move the electron beam to the next position, then the system will generate 2,304 data points approximately every 1.28 microseconds. This averages out to a rate of approximately 2 gigasamples/second. Using a collimator grid having an array of 100×100 apertures, the total amount of discrete pieces of data that is processed for a single frame, which includes the use of x-ray paths from each of the collimator apertures only once, is approximately 23,040,000 data samples.

To generate an accurate image, the read-modify-write cycle for each combination of new x-ray transmissiveness information should occur fast enough so that the information can be processed before a new set of data samples arrives. In the presently preferred embodiment, the data samples are produced at a rate that will allow a refresh rate compatible with standard video display devices. Thus, the scan processing system should have the capability to process the incoming data samples at a fast enough rate to be compatible with a video display device, as well as being fast enough to process data samples before a new set of data samples arrived from the next aperture.

When particular target assembly locations are re-scanned within a single image frame as described in the prior section, the number of data samples to be processed per frame increases as a multiple of the number of re-scans to perform. To keep from falling behind in the generation of image pixels, an embodiment of the invention includes a scan processing system to dynamically combine the pieces of x-ray transmissiveness information that pertain to the same collimator aperture/detector element pairing. The resulting x-ray transmissiveness information is then transmitted to the interface module 710 of imaging chassis 1005 for further processing, including image reconstruction processing.

Figure 9:
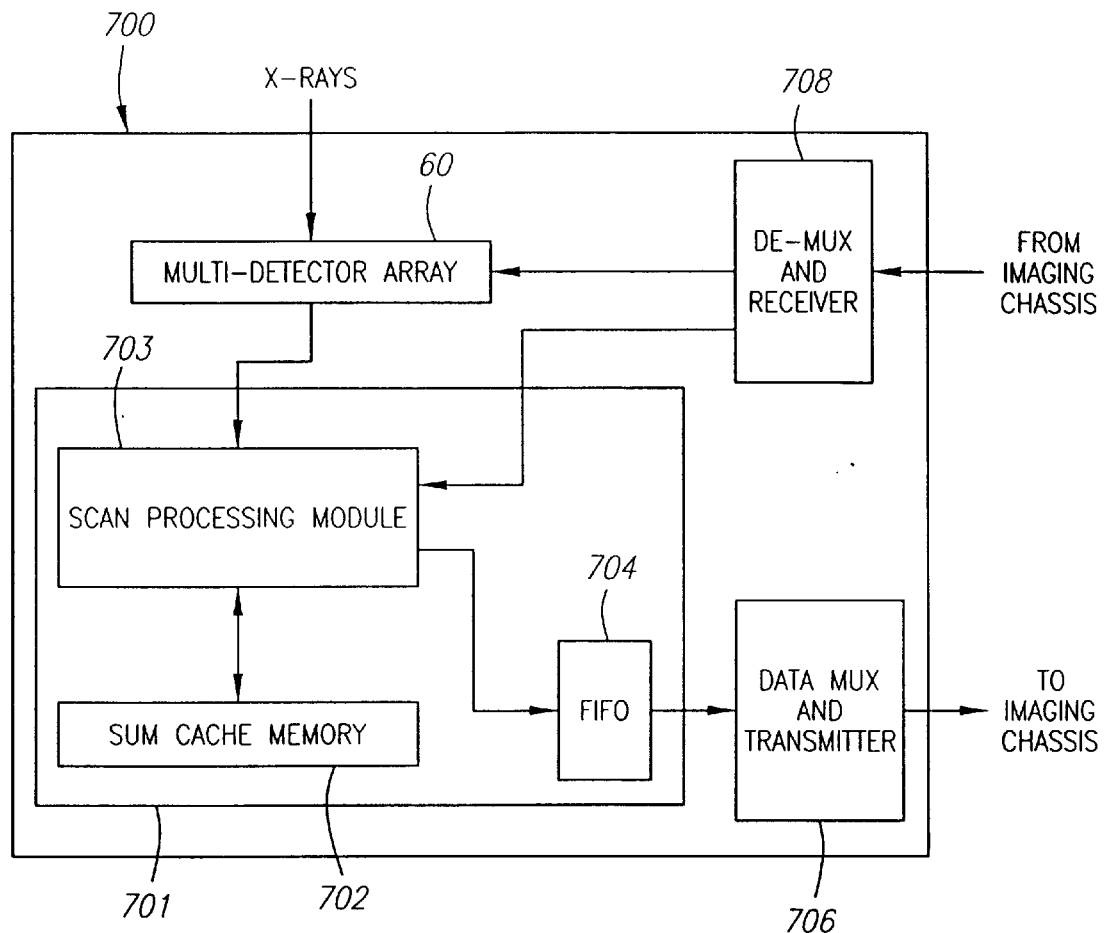
FIG. 9 is a diagram of an embodiment of a detection module.

FIG. 9 diagrams an embodiment of a detection module 700. The detection module 700 includes a multi-detector array 60 to receive x-rays that pass through the object to be imaged. As stated above, the preferred multi-detector array 60 comprises a 48 by 48 array of detector elements. Each detector element produces a signal representative of the quantity and/or magnitude of x-ray photons that strike it during a particular measurement period. In an embodiment, the x-ray transmissiveness information produced by each detector element is a three bit digital signal. The preferred multi-detector array is described in more detail in copending U.S. application Ser. No. 09/167,318, filed concurrently herewith, which is hereby incorporated by reference in its entirety.

The x-ray transmissiveness information produced by each detector element is transmitted to a scan processing system 701. According to an embodiment, scan processing system 701 comprises a scan processing module 703, a sum cache memory 702, and a FIFO 704. Scan processing module 703 comprises circuitry and/or hardware/software to sort and process the incoming data samples from the multi-detector array 60. One type of operation performed by scan processing module 703 include a data summing operation to sum x-ray transmissiveness information obtained from the same detector element for emissions from a same collimator aperture when the stepping pattern dwells the electron beam at a same position on the target assembly more than once to during a single frame. Sum cache memory 702 stored partially summed x-ray transmissiveness information during the summing operations. The completed x-ray transmissiveness information is output from the scan processing module 703 to a FIFO 704. FIFO 704 regulates the transfer of data from scan processing system 701 to a Data Mux/Transmitter 706. Data Mux/Transmitter 706 performs the operation of sending data to the interface module 710 of interference chassis 1005 (FIG. 8). Control signals for operating scan processing system 701 and multi-detector array 60 are received from interface module 710 at a De-Mux/Receiver 708.

According to an embodiment, detection module 700 can operate in a number of modes which affect whether and how the detection module 700 combines the x-ray transmissiveness information obtained from the multi-detector array 60. The choice of an operating mode also affects when the x-ray transmissiveness information is output from the detection module 700 to interface module 710.

For example, the operating modes includes an "image acquisition" mode, in which x-ray transmissiveness information from multiple x-ray illuminations within a frame which correspond to the same collimator aperture/detector element pairing are combined by the scan processing module 703. In an embodiment, x-ray transmissiveness information comprising 3-bit data from each detector element is received from the multi-detector array 60. If portions of an object are re-illuminated during a single frame, then related items of 3-bit data are summed by the scan processing module 703 to generate 4 bit x-ray transmissiveness information used to for image reconstruction.

A second mode is a "sensor" mode in which 3-bit data from the multi-detector array 60 is directly transmitted to the imaging chassis 1005. The sensor mode can be used as a diagnostic mode, in which only specific collimator apertures are illuminated upon a specific timing control signal.

A third mode is an "image test" mode. In the image test mode, x-ray transmissiveness information is combined in the same way as in the image acquisition mode. However, the summed x-ray transmissiveness information is output to the imaging chassis 1005 only after a timing control signal associated with a specific scanned collimator aperture is received.

Another mode is an "alignment" mode, which is used to align the multi-detector array 60 with the apertures of the collimator grid 70. In the alignment mode, when 3-bit values are generated by the detector elements of an 48 by 48 multi-detector array 60, 48 nine-bit values are transmitted for each collimator aperture. Each of these nine-bit values represent the sum of 48 detector elements for a single illumination through a collimator aperture. The 48 nine-bit values are further summed to provide a 15-bit value representing the total intensity received at all the detector elements for a single illumination of a collimator aperture. According to a method of performing alignment, successive illuminations can be performed against particular collimator apertures when adjusting the relative positioning between the collimator grid 70 and multi-detector array 60. The maximum intensity value measured by the multi-detector array 60 in alignment mode identifies an optimal alignment position of the components of the imaging system.

Figure 10:
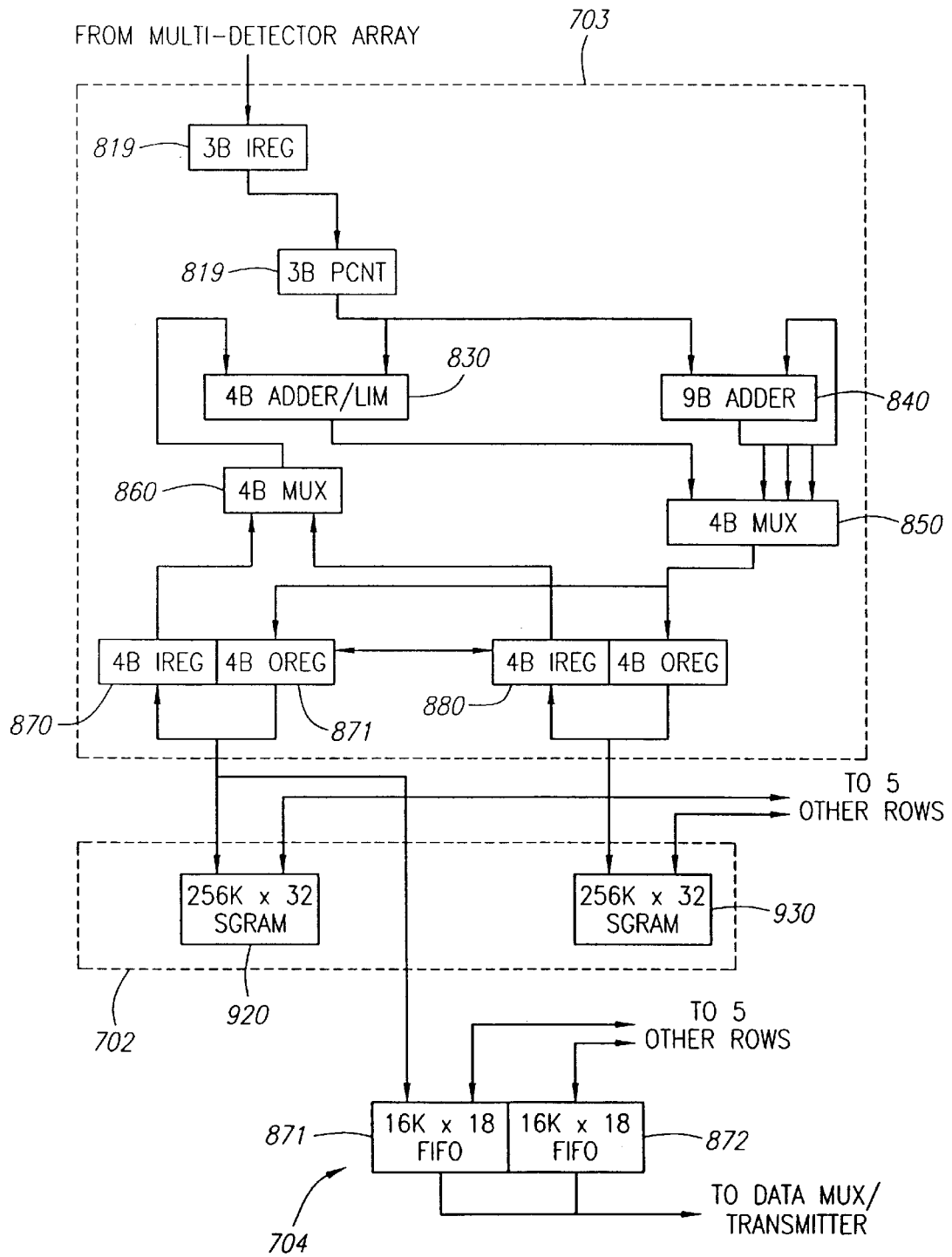
FIG. 10 is a diagram of a scan processing system according to an embodiment of the invention.

Referring to FIG. 10, shown are components of a scan processing system 701 according to an embodiment of the invention. In the present embodiment, the circuitry of FIG. 10 processes data received from a single row of detector elements. Six such circuits can be organized in parallel to receive and process data from six rows of detector elements. If the imaging system employs a 48 by 48 array of detector elements, then eight such groups of parallel circuitry can be employed to receive and process data from all 48 rows of detector elements.

In FIG. 10, 3-bit x-ray transmissiveness information from a single row of detector elements is received at an input register 819. The input register 819 provides the x-ray transmissiveness information to a counter 820.

If the detection module 700 is in image acquisition mode, the x-ray transmissiveness information is sent from counter 820 to an adder 830. At adder 830, the current x-ray transmissiveness information is added to prior x-ray transmissiveness information that was generated as a result of one or more prior x-ray emissions from the same collimator aperture in the same frame. The resulting output from adder 830 is provided to multiplexor 850, which then provides the summed x-ray transmissiveness information (through output registers 871 or 881) to either sum cache memory 702 or FIFO 704. If there are no more re-scans to be performed in the frame for the collimator aperture corresponding to that summed x-ray transmissiveness information, then the summed x-ray transmissiveness information is sent to the FIFO 704 for transmission to the interface module 710 of imaging chassis 1005 (FIG. 8). If additional re-scans are to be performed, then the summed x-ray transmissiveness information is sent to the sum cache memory 702.

The sum cache memory 702 is used to temporarily store partially summed data from multiple passes of scan lines in a single frame. The sum cache memory should be large enough to contain the partially summed information for the number of rows of collimator apertures being processed. For example, if the scanning pattern is configured such that there can be up to 16 rows of collimator apertures are partially scanned at any given time, then the sum cache memory 702 should be capable of supporting up to 16 rows of partially summed data. In an embodiment, the sum cache memory 702 comprises memory components that can hold up to 16 lines×128 collimator apertures of data.

According to an embodiment, sum cache memory 702 comprises a left cache memory unit 920 and a right cache memory unit 930. Partially summed data can be stored in either the left 920 or right 930 cache memory units. In operation, partially summed data is read from one cache memory unit, is combined with additional data at the adder 830, and if the newly summed data is not yet complete, the newly summed data is thereafter stored at the other cache memory unit. The partially summed data from a prior collimator aperture in the same frame is sent to adder 830 through multiplexor 860, from either left cache memory unit 920 or right cache memory unit 930, through left input register 870 or right input register 880 respectively. Although the disclosed sum cache memory components utilize the terms "right" and "left", that terminology is merely for purposes of explanation and should not be construed as limiting in any way.

If the detection module is in alignment mode, then counter 820 sends x-ray transmissiveness information to adder 840, where it is added to prior values received from other detector elements in the same row of detector elements. According to an embodiment utilizing a multi-detector array having a 48 by 48 array of detector elements, the x-ray transmissiveness information for each row is summed into four groups. A first group for columns 1–12, a second group for columns 13–24, a fourth group for columns 25–36, and a fourth group for columns 37–48. Then, the data from groups of four rows are summed. For example, Row 1 data is summed with data from Row 7, Row 13, and Row 19. The combined information is then output in twelve cycles with the output during each cycle preferably being one set of data for twelve columns of detector elements.

FIFO 704, which preferably comprises sub-FIFO memories 871 and 872, stores x-ray transmissiveness information and outputs that information to Data Mux/Transmitter 706 (FIG. 9). Data Mux/Transmitter 706 multiplexes the x-ray transmissiveness information and then transmits that information to the interface module 710 of imaging chassis 1005 (FIG. 8).

Figure 11:
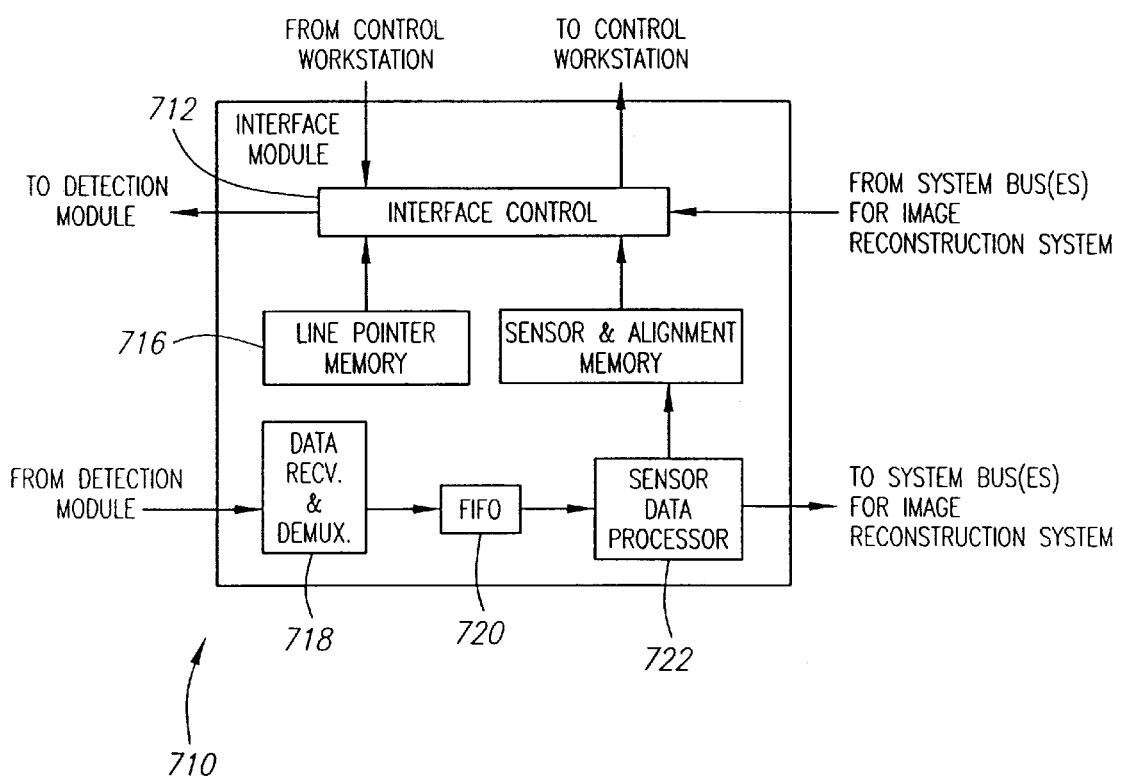
FIG. 11 is a diagram of an interface module according to an embodiment of the invention.

FIG. 11 diagrams an embodiment of an interface module 710. Signals representing x-ray transmissiveness information sent from detection module 700 to interface module 710 are received and demultiplexed by data receiver 718. The x-ray transmissiveness information received by data receiver 718 is serially fed into FIFO memory 720. FIFO memory 720 regulates the transfer of data that is sent to sensor data processor 722. If the imaging system is in image acquisition mode, then signals representing x-ray transmissiveness information is passed from sensor data processor 722 to the image pixel reconstruction modules of the image reconstruction system 65. If the imaging system is in sensor or alignment modes, then sensor data processor 722 sends x-ray transmissiveness information to a sensor and alignment memory 714. Sensor and alignment memory 714 stores information for transmission to control workstation 150. Line pointer memory 716 stores control information received from control workstation 150 that represents the order and stepping pattern of the electron beam and provides signals representing this information to detection module 700. Interface controller 712 receives and transmits signals between the interface module 710 and control workstation 150, and also transmits signals to the detection module 700.

While the embodiments, applications and advantages of the present inventions have been depicted and described, there are many more embodiments, applications and advantages possible without deviating from the spirit of the inventive concepts described herein. Thus, the inventions are not to be restricted to the preferred embodiments, specification or drawings.

What is claimed is:

1. A scan processing system for processing x-ray transmissiveness information comprising:
   a scan processing module at which related x-ray transmissiveness information from multiple x-ray illuminations of an object to be imaged by an x-ray source received by a detector comprising a plurality of detector elements, are dynamically summed;
   a random access memory at which intermediate results from said scan processing module are temporarily stored and communicated back to said scan processing module; and
   a data transmitter, said data transmitter coupled to said scan processing module for reception of image information from said scan processing module, and said data transmitter having a transmitter output communicatively coupled to an image reconstruction system.

2. The scan processing system of claim 1 wherein said random access memory comprises a plurality of cache memory units.

3. The scan processing system of claim 2 wherein said plurality of cache memory units comprises a first and a second cache memory unit.

4. The scan processing system of claim 3 wherein said intermediate results are stored by said first cache memory unit, said intermediate results are added to said related x-ray transmissiveness information by said scan processing module to generate summed x-ray transmissiveness information, and said summed x-ray transmissiveness information stored at said second cache memory unit.

5. The scan processing system of claim 1 wherein said related x-ray transmissiveness information received at said detector corresponds to x-ray transmissiveness information resulting from more than one x-ray illumination of said object from one aperture of a plurality of apertures in a collimator grid: said collimator grid positioned between said x-ray source and said detector.

6. The scan processing system of claim 1 wherein said scan processing module comprises one or more adders to sum said related x-ray transmissiveness information.

7. The scan processing system of claim 1 wherein said related x-ray transmissiveness information are summed for alignment of an x-ray imaging system.

8. The scan processing system of claim 1 wherein said related x-ray transmissiveness information are summed to generate data for use in an image reconstruction system.

9. An imaging system comprising:
   an x-ray source comprising a charged particle beam source and an x-ray target assembly, said charged particle beam source generating a particle beam that scans across said x-ray target assembly in a scanning pattern said scanning pattern rescans a portion of said x-ray target assembly a plurality of times during a frame;
   a plurality of detection elements configured to detect x-rays generated by said x-ray target assembly;
   each of said plurality of detection elements having a detection output comprising x-ray transmissiveness information; and
   a scan processing system comprising
      a scan processing module, said scan processing module configured to dynamically combine related x-ray transmissiveness information received at said plurality of detection elements; and
      a cache memory, said cache memory configured to store intermediate results from said scan processing system.

10. The imaging system of claim 9 further comprising an image reconstruction module comprising an image reconstruction module input, said image reconstruction module input communicatively connected to said scan processing system.

11. The imaging system of claim 9 wherein said related x-ray transmissiveness information are summed to generate data for use in reconstructing an image.

12. The imaging system of claim 10 wherein said cache memory comprises a plurality of cache memory units.

13. The imaging system of claim 12 wherein said plurality of cache memory units comprises a first and a second cache memory unit.

14. The scan processing system of claim 13 wherein an intermediate result from said scan processing module is stored by said first cache memory unit, said intermediate result is added to said related x-ray transmissiveness information by said scan processing module to generate summed x-ray transmissiveness information, and said summed x-ray transmissiveness information stored at said second cache memory unit.

15. The scan processing system of claim 9 wherein said related x-ray transmissiveness information received at said plurality of detection elements corresponds to x-rays received from one or more apertures of a plurality of apertures in a collimator grid.

16. The imaging system of claim 9 wherein said scan processing module comprises one or more adders.

17. The imaging system of claim 9 wherein said related x-ray transmissiveness information are summed for alignment of said imaging system.

* * * * *